United States Patent
Klitmose

(10) Patent No.: US 6,997,911 B2
(45) Date of Patent: Feb. 14, 2006

(54) MEDICATION DELIVERY DEVICE WITH REPLACEABLE COOPERATING MODULES AND A METHOD OF MAKING SAME

(75) Inventor: Lars Peter Klitmose, Gentofte (DK)

(73) Assignee: Novo Nordisk A/S, Bagsvaerd (DK)

( * ) Notice: Subject to any disclaimer, the term of this patent is extended or adjusted under 35 U.S.C. 154(b) by 0 days.

(21) Appl. No.: 09/867,277

(22) Filed: May 29, 2001

(65) Prior Publication Data

US 2002/0010432 A1 Jan. 24, 2002

Related U.S. Application Data

(60) Provisional application No. 60/210,909, filed on Jun. 12, 2000.

(30) Foreign Application Priority Data

May 30, 2000 (DK) ........................................ 2000 00852

(51) Int. Cl.
*A61M 5/00* (2006.01)

(52) U.S. Cl. ..................................................... 604/232
(58) Field of Classification Search ................ 604/232, 604/132, 139, 148, 151, 152–154, 30–33, 604/35, 65–67, 80–81, 118, 123, 187, 200, 604/201, 891.1; 128/DIG. 1, DIG. 12, DIG. 13
See application file for complete search history.

(56) References Cited

U.S. PATENT DOCUMENTS

| | | | | |
|---|---|---|---|---|
| 4,741,736 A | * | 5/1988 | Brown ........................ | 604/134 |
| 4,978,335 A | | 12/1990 | Arthur, III | |
| 5,088,981 A | * | 2/1992 | Howson et al. ................ | 604/31 |
| 5,256,157 A | * | 10/1993 | Samiotes et al. ........... | 604/246 |
| 5,590,648 A | * | 1/1997 | Mitchell et al. ............ | 128/630 |
| 5,593,390 A | * | 1/1997 | Castellano et al. ......... | 604/187 |
| 5,643,212 A | | 7/1997 | Coutré et al. | |
| 5,651,775 A | * | 7/1997 | Walker et al. .............. | 604/207 |
| 5,658,250 A | * | 8/1997 | Blomquist et al. ............ | 604/65 |
| 5,713,856 A | * | 2/1998 | Eggers et al. ................. | 604/65 |
| 5,836,904 A | * | 11/1998 | Cooper ........................ | 602/60 |
| 5,898,783 A | * | 4/1999 | Rohrbach ................... | 340/5.31 |
| 5,925,021 A | | 7/1999 | Castellano et al. | |
| 5,935,099 A | * | 8/1999 | Peterson et al. .............. | 604/65 |
| 6,066,243 A | * | 5/2000 | Anderson et al. ........... | 204/403 |
| 6,110,152 A | * | 8/2000 | Kovelman ................... | 604/232 |
| 6,302,855 B1 | * | 10/2001 | Lav et al. ................... | 600/584 |
| 6,558,320 B1 | * | 5/2003 | Causey, III et al. ........ | 600/300 |

FOREIGN PATENT DOCUMENTS

| WO | WO/95/24233 | 9/1995 |
|---|---|---|
| WO | WO/99/59657 | 11/1999 |

* cited by examiner

*Primary Examiner*—Kevin Shaver
*Assistant Examiner*—Anu Ramana
(74) *Attorney, Agent, or Firm*—Marc A. Began, Esq.; Reza Green, Esq.; Richard W. Book, Esq.

(57) ABSTRACT

The invention relates to: A medication delivery device and a method of making such a device. The object of the present invention is to provide a handy medication delivery device that may be easily adjusted to the different needs of a given user in different situations and to the different needs of different users, and which is economic from a production point of view. The problem is solved in that it comprises a basis module (1) and one or more replaceable modules (2, 3, 4, 5, 6), each of which is adapted to cooperate mechanically and/or electronically with the basis module to provide a specific function, and the basis module includes resources that are jointly used by the replaceable modules. This has the advantage of providing a rational concept for economically supplying high quality, mass-produced devices capable of being customized to individual users' needs for functionality by avoiding the duplication of key components. The invention may be used in injector type, medication pump type, inhaler or spray type devices for delivering a discrete dose or a continuous dose of a medication to a user.

3 Claims, 6 Drawing Sheets

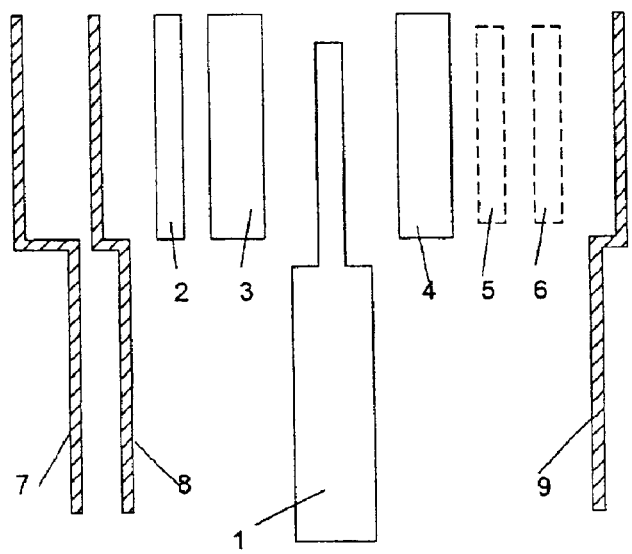
Fig. 1.a
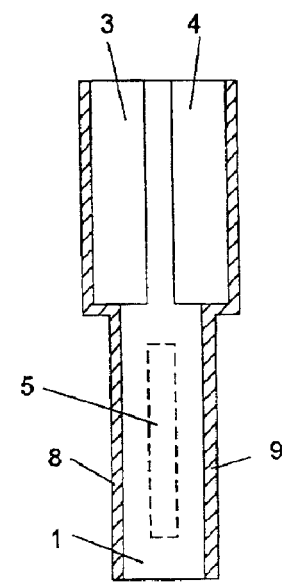
Fig. 1.b
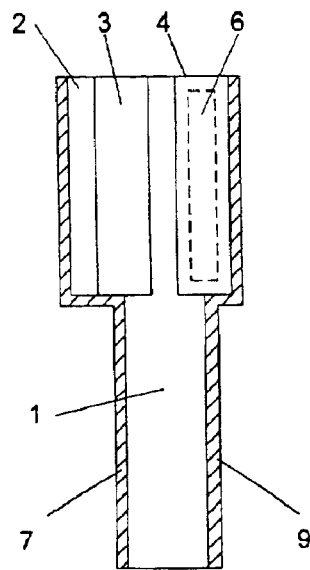
Fig. 1.c

MEDICATION DELIVERY DEVICE WITH REPLACEABLE COOPERATING MODULES AND A METHOD OF MAKING SAME

This application claims the benefit of provisional application No. 60/210,909, filed Jun. 12, 2000.

THE TECHNICAL OF THE INVENTION

The invention relates to drug administration systems for medical self-treatment.

The invention relates specifically to: A medication delivery device.

The invention furthermore relates to: A method of making a medication delivery device.

DESCRIPTION OF RELATED ART

For people who frequently have to take medicine using some sort of delivery device, different options as regards treatment may be convenient in different situations.

Further, for a producer of a medication delivery device, it is of importance to be able to customize the devices to the needs and wishes (including more design oriented 'functionality') of any potential buyer of the product and at the same time achieve economies of scale.

U.S. Pat. No. 5,925,021 discloses a medication delivery device that uses a microprocessor and a display to record, analyze and visualize various data concerning the medication administration. A single, all-in-one device that performs a variety of functions is provided.

WO-A-99/59657 discloses a medical apparatus for use by a patient for medical self-treatment of diabetes. The various functional units are physically tied together in a compact device. During use, each functional unit is employed individually.

DISCLOSURE OF THE INVENTION

The problem of the prior art is that the multifunction devices provide more functions than are needed in a certain situation and may thus be complicated to operate or more voluminous or more expensive than necessary, etc. The devices comprising non-cooperating, physically coupled individual units that are employed individually may be handy to take with you and ensure that you bring the necessary functional units, but are inconvenient in use in that they have to be mechanically separated and handled independently.

The object of the present invention is to provide a handy medication delivery device that may be easily adjusted to the different needs of a given user in different situations and to the different needs of different users, and which is economic from a production point of view.

This is achieved according to the invention in that it comprises a basis module and one or more replaceable modules each of which is adapted to cooperate mechanically and/or electronically with the basis module to provide a specific function, and the basis module includes resources that are jointly used by the replaceable modules In the present context, the term 'medication delivery device' is taken to mean, an injector type device (such as a pen injector or a jet injector) for delivering a discrete dose of a liquid medication (possibly in the form of small drops), a medication pump for continuous delivery of a liquid medication, an inhaler, spray or the like for delivering a discrete or continuous dose of a medication in vaporized, 'atomized' or pulverized form.

In the present context, the term 'replaceable module' is taken to mean that said module may be conveniently added to or removed from the basis module according to the user's needs in a given situation. I.e. each replaceable module may be interchanged with a different replaceable module, which together with the basis module provides a different function. Further, a producer of medication delivery devices will be able to tailor several different 'models' of devices based upon the same basis module (or basis modules) by combining it with one or more replaceable modules from a collection of 'standard' modules and achieve the combined benefits of using standard components (or building blocks) and still being able to do it in an economic way. Further, due to the modular way of building the devices, each module having a standard mechanical and (if relevant) electrical interface to the basis module and to other replaceable modules, it is possible for a user to buy a minimum configuration device according to his or her present needs and then to 'upgrade' the device along the way.

The basis module comprises basic elements of a medication delivery device. Some of or all of the basic elements of the basis module may be utilized by the different replaceable modules to provide different functions.

The possibility to flexibly configure the medication delivery device according to need has the following combined advantages:

- It makes possible the fulfillment of the needs of an individual user originating from short-term changes such as use at home vs. use out of home and from longer-term changes due to changes in the treatment, development of new functional modules etc.
- It makes it possible to build the production of medication delivery devices around a limited number of functional modules. This provides a rational concept for economically delivering high quality, mass-produced devices capable of being customized to individual user's needs for functionality by avoiding the duplication of key components, while still keeping the modular structure of the device.

When the basis module at least comprises means for holding a medication cartridge, means for transferring a part of or all of a medication contained in said medication cartridge from said medication cartridge to a user, means for receiving one or more replaceable modules, and means for supplying electric energy to the basis module and to the replaceable modules, it is ensured that the basic components for delivering a dose to a user from a medication cartridge, including means for energizing the transfer of the medication to a user and for supplying electric energy to all other electrical components in the basis module and in the replaceable modules, are provided.

When the basis module further comprises electronic means for monitoring and controlling the medication delivery process and for communicating with replaceable modules and with the user, it is ensured that the individual functions may be electronically driven and controlled, which generally improves reliability and accuracy, and that data from different functional modules may be combined with user input to produce intelligent results and improve user comfort and safety, and that a history of the drug administration process may be generated.

In a preferred embodiment said medication cartridge is replaceable and has an outlet and a movable wall, which, when displaced in the direction of the outlet, forces the contents out of the cartridge through said outlet.

When the outlet of said medication cartridge is connected to a replaceable catheter, and said means for transferring medication to a user is adapted to work in a continuous mode, so that medication is forced out of the cartridge through the outlet of said catheter, it is ensured that a continuous dose profile may be delivered to a user.

In a preferred embodiment said means for transferring a part of or all of the medication from said medication cartridge to the user at least comprise a piston rod being operable to engage and displace said movable wall, electrically driven actuating means, and driving means for transferring movement from said electrically driven actuating means to said piston rod.

When said means for receiving the replaceable modules comprise means for mechanically receiving and fixing said replaceable modules to the basis module, and means for electrically connecting said replaceable modules to electronic means of the basis module and to said means for supplying electric energy, it is ensured that a 'standard' interface for coupling the replaceable modules mechanically and electrically to the basis module is provided. If the energizing means are provided in the form of a battery pack, it is ensured that the device may be used when 'on the move', and that the supply of energy may be provided using standard battery techniques (based on rechargeable or non-rechargeable batteries) as e.g. developed for mobile telephones.

In a preferred embodiment electronic means for monitoring and controlling the medication delivery process and for communicating with replaceable modules and with the user are contained in a replaceable module themselves.

When said electronic means at least comprise means for controlling a delivered dose by controlling the displacement of the movable wall with said piston rod, through a control of the electrically driven actuating means via the driving means for transferring movement from said electrically driven actuating means to said piston rod, and means for monitoring the volume of delivered medication corresponding to said displacement of said movable wall, means for inputting data from the user, memory means for storing data, means for communicating with the replaceable modules, means for controlling the function of the basis module and the replaceable modules, processing means for processing input data, for processing data received from the replaceable modules and for processing data stored in said memory means, and a display for visualizing said data, it is ensured that the delivered dose is electronically controlled allowing an improved accuracy compared to a purely mechanical solution, and that a register of the used medication over time and the currently remaining volume of medication in the cartridge, etc. may be generated. It further ensures that information from the various functional modules of the delivery device and from the user input may be centrally stored and analyzed and that control signals for each individual replaceable module may be transferred on the basis hereof and relevant information be presented to the user. It further ensures that a check of the correct function of each replaceable module of the delivery device and the cooperation with the basis module may be performed and that an alarm may be issued or the intended action blocked in case the result of the check is negative.

When said electronic means include means for reading an item of information on a replaceable medication cartridge when said cartridge is placed in said means for holding a replaceable medication cartridge, and means for processing said item of information, it is ensured that the process of reading and checking the contents of the medication cartridge may be automated resulting in a higher degree of safety in the handling of the medication.

When said electronic means are adapted to receive a user-specific unit containing user data, functional check procedures and user authorizing procedures, it is ensured that a check of the correct function of each replaceable module of the delivery device and the cooperation with the basis module and a check of the user ID to prevent unauthorized use of the delivery device may be provided in a single, possibly exchangeable unit customized to the actual user specific data, the present configuration of the device, and optionally containing data indicating which functionality the user has a license to. Alternatively, the processing means may be adapted to identify the present configuration of the device in terms of basis module and replaceable modules including software, when the power is turned on.

In a preferred embodiment said user-specific unit is a chip card.

When the replaceable modules may be chosen from a group consisting of
- a replaceable module containing a system for blood glucose monitoring;
- a replaceable module containing a system for continuously measuring blood glucose;
- a replaceable module containing a modem for allowing communication with a data communications network;
- a replaceable module containing a communications interface for wireless communication with other devices;
- a replaceable module containing fixed wire interfaces for communication with one or more of a personal computer, a camera, a TV-monitor, an acoustic device, a telephone, a mobile telephone;
- a replaceable module containing the functionality of a mobile telephone;
- a replaceable module containing a loudspeaker;
- a replaceable module containing a microphone, a loudspeaker and a processor and software for speech recognition for providing a voice interface;
- a replaceable module containing means for monitoring the temperature of the medication cartridge and its contents;
- a replaceable module containing means for monitoring and controlling the temperature of the medication cartridge and its contents;
- a replaceable module containing means for providing a selectable acoustic or vibratory or optical signal after a certain settable time or on the occurrence of a certain event;
- a replaceable module containing means for vibrating the contents of the medication cartridge, and means for providing an a arm signal indicating the elapsing of a settable time Lo ensure a proper mixing of the constituents of the medication cartridge;
- a replaceable module containing means for detecting shaking movements of the medication delivery device and means for providing an alarm signal indicating that a certain amount of shaking movements has been performed to ensure a proper mixing of the constituents of the medication cartridge;
- a replaceable module containing software for controlling the medication delivery at settable velocities, controlled time scales, maximum delivered doses, etc.;
- a replaceable module containing software for generating a log of certain user defined events monitored by the medication delivery device;
- a replaceable module containing software for controlling a user ID;

a replaceable module containing a display adapted for left-handed use;

a replaceable module containing a display adapted for right-handed use;

a replaceable module containing means for delivering a specific dose profile to a user through a catheter by controlling said means for transferring the medication in such a way that a continuous pump mode is provided, it is ensured that the medication delivery device may be configured to a wide range of functionally different devices based upon standardized building blocks.

When the basis module and the replaceable modules are provided with replaceable covers, it is ensured that the design or look of the medication devices may be adjusted to the instant user wishes, e.g. to match a dress or the like.

When the basis module contains functionality that may be locked and made available to the user only by a unique software key and/or a software update, it is ensured that several functions may be provided in a single module, if appropriate, the use of each function being dependent of the input of a specific key word and/or a software update. This could be of relevance in connection with certain functions that are related/overlapping in hardware and or/software implementation.

A method of making a medication delivery device is furthermore provided by the present invention. When it comprises the steps of (a) defining and constructing a basis module containing common resources, and (b) defining and constructing one or more replaceable modules each of which being adapted to cooperate mechanically and electronically with the basis module to provide a specific function, and (c) deciding a configuration of functions according to need, based on a selection of possible functions, and (d) composing a device implementing the decided functions by combining the relevant basic module and one or more replaceable modules, possibly repeating steps (c) and (d), in case of changing functionality needs, the same advantages as disclosed above for claim 1 are achieved.

When the steps of deciding a configuration of functions according to need and composing a device implementing the decided functions are performed by a user of the device, it is ensured that the fulfillment of the needs of an individual user originating from short-term changes such as use at home vs. use out of home and from longer-term changes due to changes in the treatment, development of new functional modules etc. are made possible.

When the steps of deciding a configuration of functions according to need and composing a device implementing the decided functions are performed by a producer or supplier of the device, it is possible to build the production of differently configured medication delivery devices around a limited number of functional modules. This provides a rational concept for economically delivering high quality, mass-produced devices capable of being customized to individual user's needs for functionality by avoiding the duplication of key components.

When it further comprises the step of locking the device so that it cannot be separated into its constituent modules by a user, the responsibility for a correct function of the final device as delivered may be guaranteed by the producer/supplier of the device without performing special check routines prior to each use of the device.

BRIEF DESCRIPTION OF THE DRAWINGS

The invention will be explained more fully below in connection with a preferred embodiment and with reference to the drawings in which:

FIG. 1 shows an injection device according to the invention,

The figures are schematic and simplified for clarity, and they just show details, which are essential to the understanding of the invention, while other details are left out. Throughout, the same reference numerals are used for identical or corresponding parts.

DETAILED DESCRIPTION OF EMBODIMENTS

Figure 2:
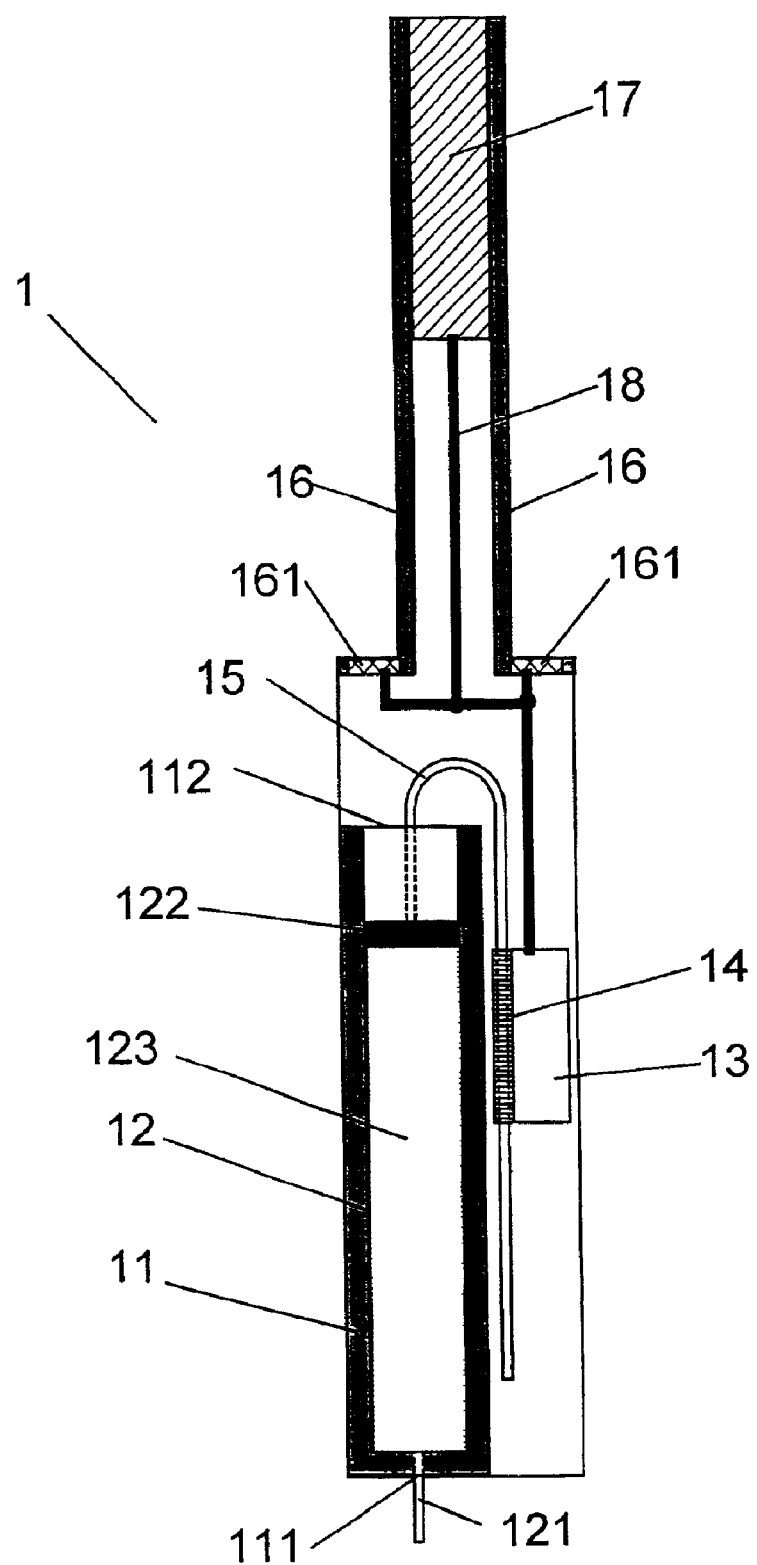
FIG. 2 shows a preferred embodiment of a basis module according to the invention including basic resources for dosing.

A module based on an electromechanical unit for moving a piston rod to move a piston in a replaceable cartridge with an outlet and a processing unit for controlling the medication delivery process etc. together with I/O-components is the base unit in the following embodiments of the invention on which different replaceable modules can be attached to give different applications, such as BGM, voice interface for visually disabled persons, etc.

FIG. 1 shows an injection device according to the invention illustrating its modular construction.

FIG. 1a shows the basis module 1 containing basic mechanical and electrical resources necessary for the delivery process and the control hereof and various replaceable modules 2, 3, 4, 5, 6 each of which, together with the resources of the basis module, implement a specific function. The replaceable modules may consist of hardware (and optionally software) 2, 3, 4 or be pure software modules 5, 6. Special cover modules for defining the visual impression of the medication delivery device are shown 7, 8, 9. The covers may have different colors, be made of different materials have different surfaces and forms. Covers may be mounted during production so that the device comes with standard or pre-selected covers, which may then later be replaced with other covers according to the user's preferences. The materials of the covers may have different special properties, e.g. elastic or luminescent or water repellant etc. The covers may constitute a water-resistant or watertight enclosure of the medication delivery device.

In FIG. 1b a medication delivery device consisting of a basis module 1, two replaceable hardware modules 3, 4, and a software module 5 loaded into a memory of the basis module is shown. The device is finished with cover modules 8, 9.

In FIG. 1c a medication delivery device consisting of a basis module 1, three replaceable hardware modules 2, 3, 4, and a software module 6 loaded into a memory of replaceable module 4 is shown. The device is finished with cover modules 7, 9.

The medication delivery devices in FIGS. 1.b and 1.c may be built together by the user of the device according to his or her present needs or alternatively by the supplier of the device.

FIG. 2 shows a preferred embodiment of a basis module according to the invention including basic resources for dosing.

FIG. 2 shows an embodiment of a basis module 1 for an injection device of the pen type according to the invention, in which a cylindrical replaceable medication cartridge 12 having an outlet 121 at one end and a lid that is formed as a piston 122 at the opposite end is placed in corresponding receiving means 11. The receiving means have an opening 111 at one end for the outlet 121 of the cartridge 12 and an opening 112 at the other end for the piston rod 15. The piston rod, which is adapted to interact with the piston to displace the piston, is formed with a 180 degree bend to allow a more compact construction. It might as well, however, be implemented as a normal straight piston rod. An electric motor 13, powered from a battery or battery pack 17 via electrical conductors 18 engage with driving means 14 and corresponding driving means (not shown) on the piston rod to displace the piston rod in its axial direction, thereby displacing the piston and forcing the medication out of the cartridge through the outlet 121. In FIG. 2, the basis module is adapted for an injection device of the pen type, the outlet taking the form of a disposable needle, but it might as well take the form of a small disposable tube in the case of a jet injector. The piston rod 15 is cylindrical, axially stiff, but radially salient and provided with a thread (not shown) that together with a corresponding driving nut provided with a gear wheel (not shown) on its outer periphery and a corresponding cooperating gear wheel (not shown) on the motor constitute the driving means 14 for transferring movement from the motor 13 to the piston rod 15. The means 16 for receiving the replaceable modules (e.g. 2, 3, 4 of FIG. 1) include electric interfaces 161 in the form of one or more connectors for power feeding the replaceable modules via electrical conductors 18 and for allowing the transfer of data between the basis module and the replaceable modules (cf. FIG. 3).

Figure 3:
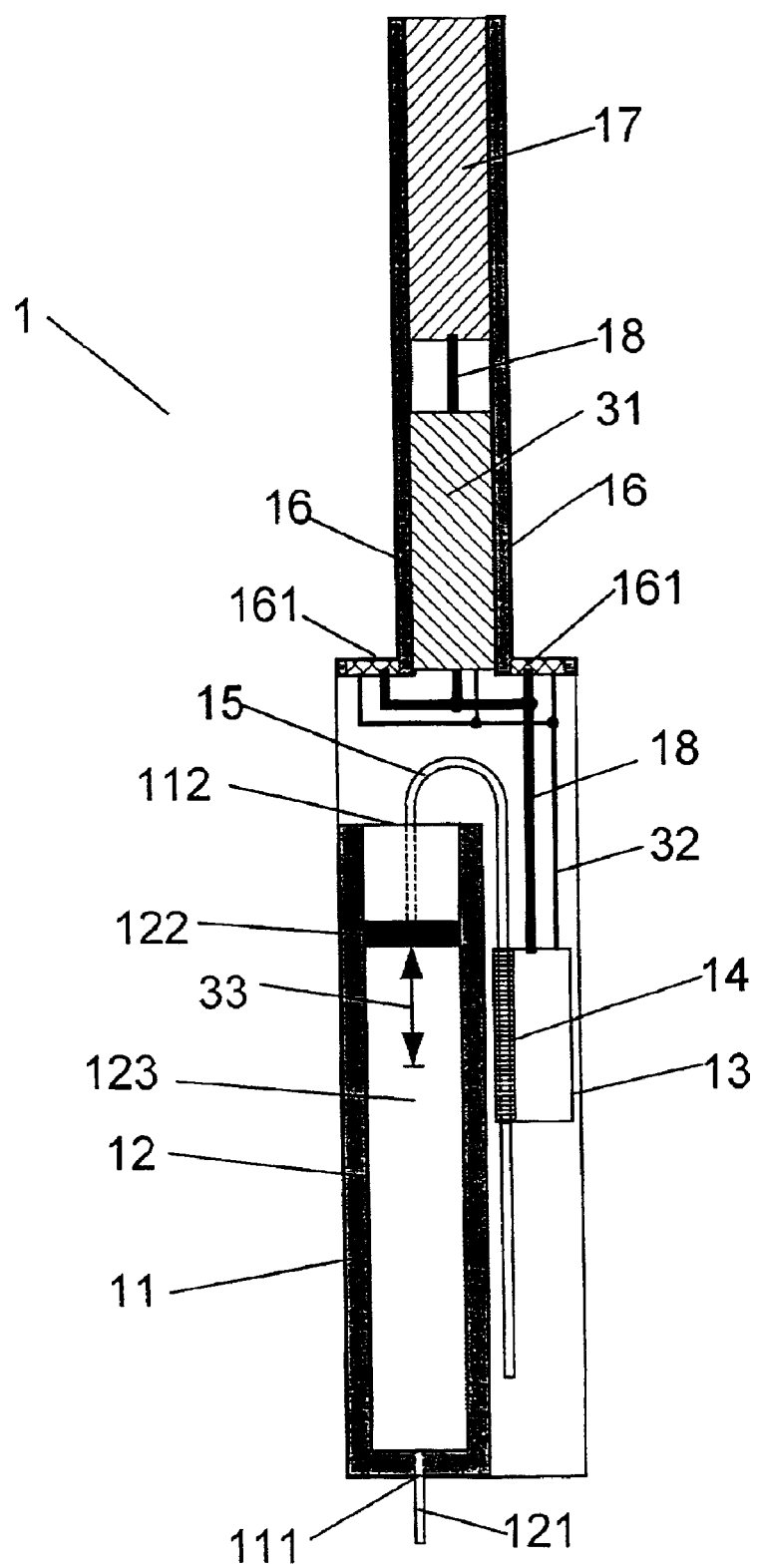
FIG. 3 shows a preferred embodiment of a basis module according to the invention including basic resources for dosing as well as electronic processing means.

FIG. 3 shows a preferred embodiment of a basis module according to the invention including basic resources for dosing as well as electronic processing means.

In addition to the features of FIG. 2, FIG. 3 contains electronic means 31 for monitoring and controlling the medication process and for communicating with the replaceable modules (e.g. 2, 3, 4 of FIG. 1) and with a user. Electrical wire connections 32 for transmitting and receiving signals to and from the replaceable modules and the electric motor are included from the electronic means 31 to the electric interfaces 161 to the replaceable modules and to the motor. The electronic means 31 include processing means (311 on FIG. 4) that are adapted to control the process of delivering a precise dose according to a given specification by controlling the displacement 33 of the piston through an accurate displacement of the piston rod by means of the electric motor 13 and the driving means 14.

Figure 4:
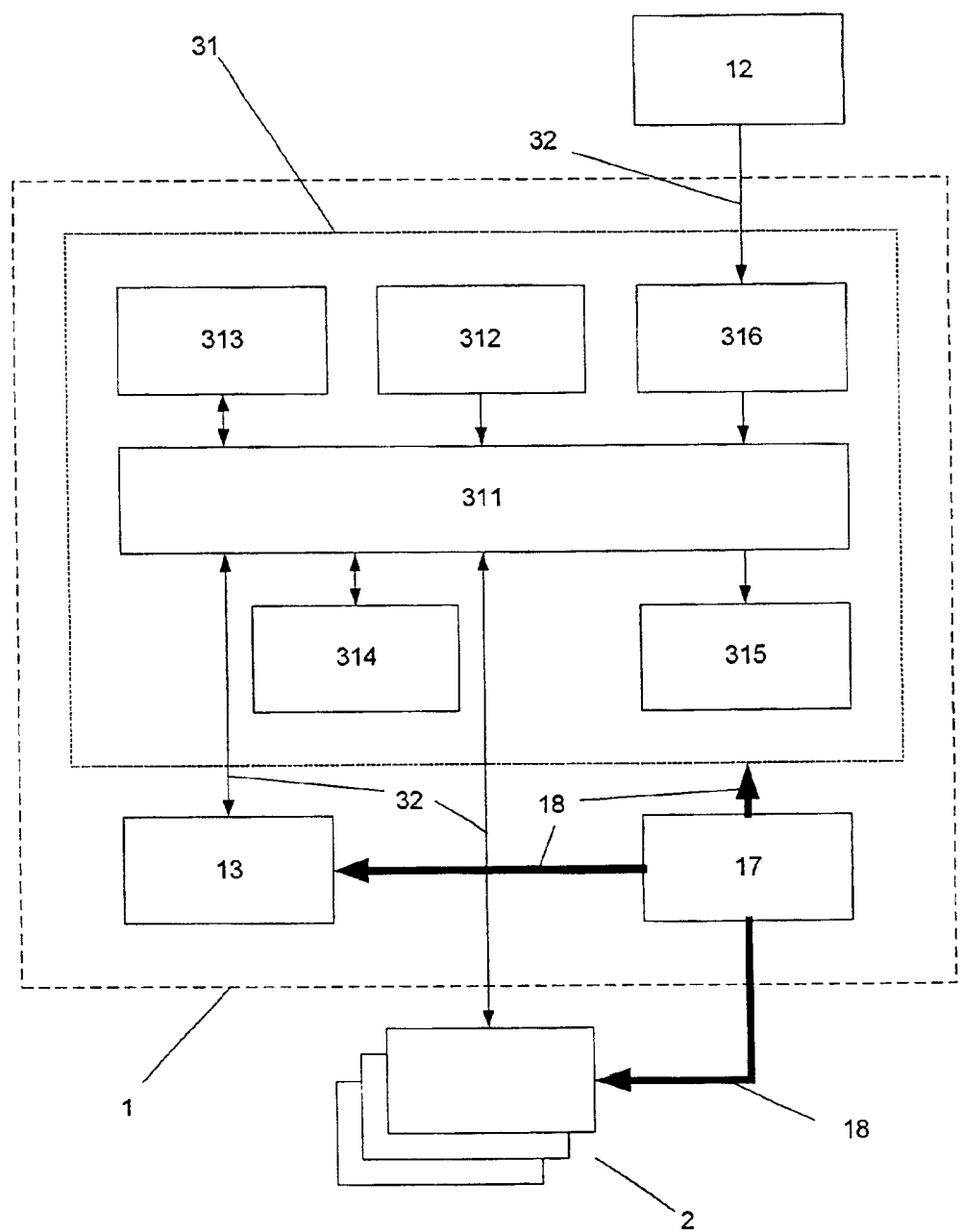
FIG. 4 shows electronic means of a basis module for controlling the medication delivery process and for communicating with the replaceable modules and with a user.

FIG. 4 shows electronic means of a basis module for controlling the medication delivery process and for communicating with the replaceable modules and with a user.

The electronic means 31 of a basis module according to the invention comprise a processor 311, memory means 313 (volatile (e.g. RAM) as well as non-volatile), a display 315 for showing user inputs and processed results to the user, means 316 for reading an item of information on a medication cartridge 12, a user input device 312 (e.g. a, possibly limited, keyboard) for inputting data from a user and a control unit 314 containing user-specific data and optionally functional check procedures and a user authorization procedure, possibly in the form of a chip card (like a SIM card of a mobile telephone). The battery 17 and its connections 18 for powering the electronic means 31 and the electric motor 13 and the replaceable modules 2 are also shown in FIG. 4 together with the signal wires 32 for communication between the processor 311, the motor 13 and the replaceable modules and for transferring an item of information from a cartridge 12 to a corresponding reading device 316.

Figure 5:
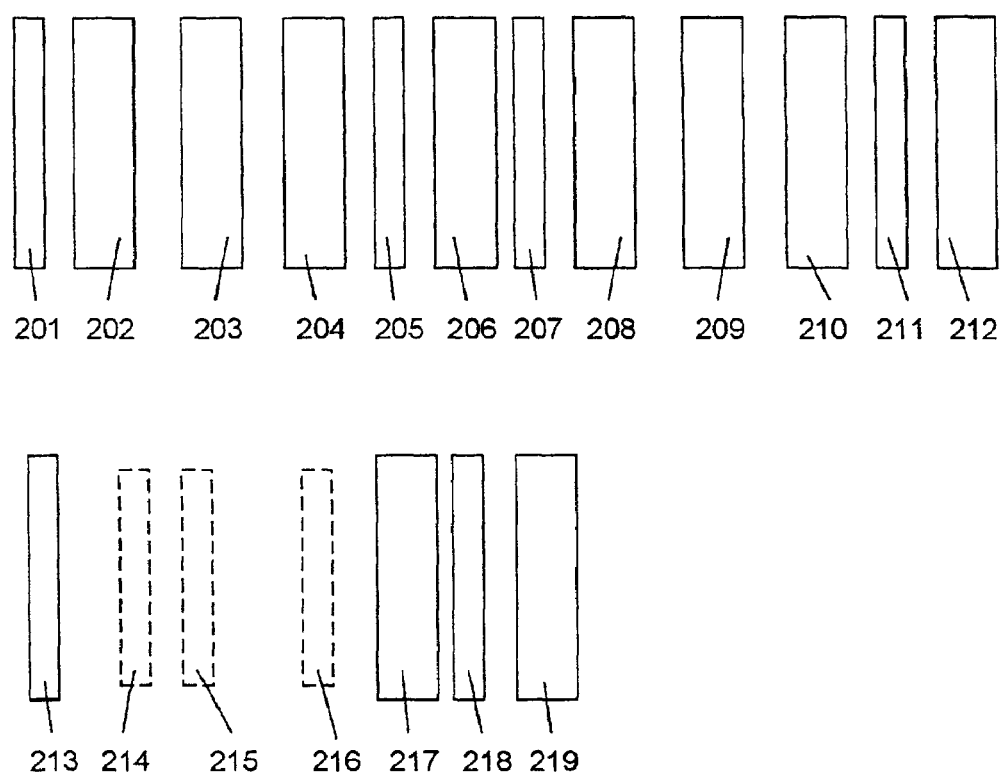
FIG. 5 shows a selection of replaceable modules according to the invention.

FIG. 5 shows a selection of replaceable modules according to the invention.

FIG. 5 sketches various replaceable modules from which a medication delivery device according to the invention may be composed in combination with a basis module (cf. 1 in FIGS. 1–3). The replaceable modules, which are briefly described in the following with reference to FIG. 5, only represent examples and does not provide an exhaustive list of relevant modules within the scope of the invention:

A replaceable module 201 containing a system for blood glucose monitoring.

A replaceable module 202 containing a system for continuously measuring blood glucose.

A replaceable module 203 containing a modem for allowing communication with a data communications network such as the Internet or any other local or global data communications network. This module may be used for downloading software to the device, for remote check of the functionality of the device, for remote diagnostics, for enabling user authorization, etc.

A replaceable module 204 containing a communications interface for wireless communication with other devices. This module implements one or more of the standards for wirelessly communicating with other devices, e.g. the Bluetooth-standard, a wirelss modem, infrared communication, etc.

A replaceable module 205 containing fixed wire interfaces for communication with one or more of a personal computer, a camera, a TV-monitor, an acoustic device, a telephone, a mobile telephone. The module includes the relevant electrical connector interfaces.

A replaceable module 206 containing the functionality of a mobile telephone.

A replaceable module 207 containing a loudspeaker.

A replaceable module 208 containing a microphone, a loudspeaker and a processor and software for speech recognition for providing a voice interface. This module implements a voice interface, e.g. For visually disabled persons.

A replaceable module 209 containing means for monitoring the temperature of the medication cartridge and its contents. This module is e.g. aimed at providing a user with information about the minimum and maximum temperatures, to which the currently loaded medication cartridge has been exposed, in order to decide whether it is usable.

A replaceable module 210 containing means for monitoring and controlling the temperature of the medication cartridge and its contents. This module is e.g. aimed at ascertaining that the currently loaded medication is usable, irrespective of the temperatures that the device experiences (within certain limits).

A replaceable module 211 containing means for providing a selectable acoustic or vibratory or optical signal after a certain settable time or on the occurrence of a certain event. This module is aimed at helping the user to observe a certain given pattern of treatment over time.

A replaceable module 212 containing means for vibrating the contents of the medication cartridge, and means for providing an alarm signal indicating the elapse of a settable time to ensure a proper mixing of the constituents of the medication cartridge.

A replaceable module 213 containing means for detecting shaking movements of the medication delivery device and means for providing an alarm signal indicating that a certain number of shaking movements has been performed to ensure a proper mixing of the constituents of the medication cartridge.

A replaceable module 214 containing software for controlling the medication delivery at settable velocities, controlled time scales (for possible use with replaceable module 211), maximum delivered doses, etc. The module is aimed at controlling the medication delivery process as regards the speed profile of the delivery, the (minimum and maximum) time between deliveries, the volume of the delivered dose, etc.

A replaceable module 215 containing software for generating a log of certain user defined events monitored by the medication delivery device. Such relevant events are time of drug deliveries, corresponding volumes, possibly temperature of the medication, possibly user inputs of relevant information to a given delivery (physical/mental stress, etc.).

A replaceable module 216 containing software for controlling a user ID by requiring the user to input a predefined sequence of characters to prevent unauthorized use of the device.

A replaceable module 217 containing a display adapted for left-handed use.

A replaceable module 218 containing a display adapted for right-handed use.

A replaceable module 219 containing means for delivering a specific dose profile to a user through a catheter having a needle at one end and whose other end is connected to the outlet of the medication cartridge, by controlling the means for transferring the medication in such a way that a continuous pump mode is provided. This module is aimed at a situation where a delivery of medication is required over a certain amount time (as opposed to an injection-type delivery, being typically of a duration of a few seconds).

Figure 6:
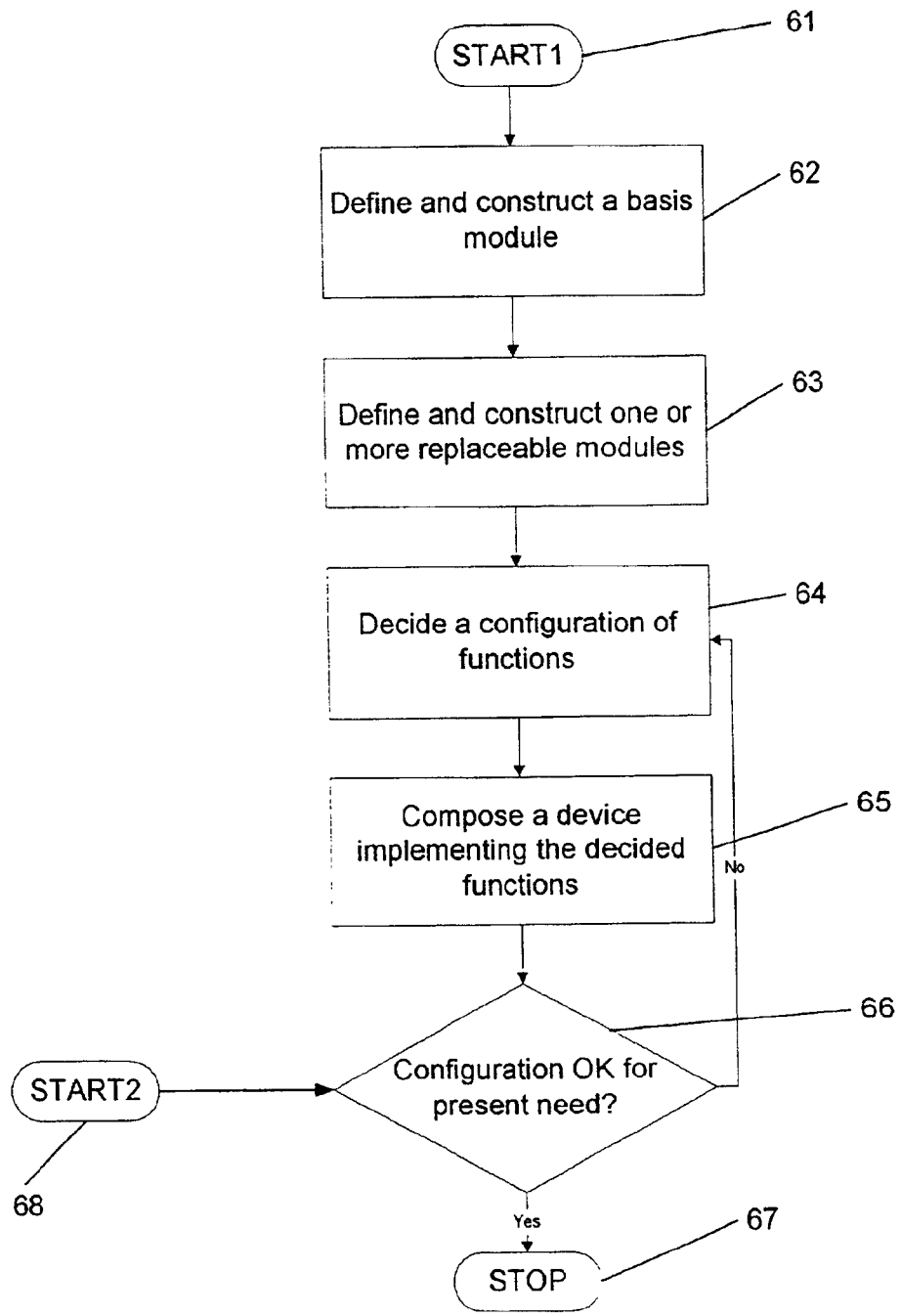
FIG. 6 shows a preferred embodiment of a method according to the invention.

FIG. 6 shows a preferred embodiment of a method according to the invention.

FIG. 6 illustrates a method of making a medication delivery device in a modular fashion. The process is started 61 by performing the step 62 of defining and constructing a basis module containing basic components and common resources as illustrated in FIGS. 1–4. In parallel hereto or subsequently, the step 63 of defining and constructing one or more replaceable modules, each of which being adapted to cooperate mechanically and electronically with the basis module to provide a specific function, is performed. Examples of such replaceable modules are discussed above in connection with FIG. 5. Subsequently, the step 64 of deciding a configuration of functions according to need, based on a selection of possible functions (e.g. among those represented by the replaceable modules just mentioned) is performed. This step may be carried out by a user sorting out a relevant configuration for a given situation or by a producer or supplier of the devices in the process of defining the relevant functions of devices to fulfill the needs of a specific customer segment. Subsequently, the step 65 of composing or building a device implementing the decided functions by combining the relevant basic module and one or more replaceable modules (such as those outlined above and sketched in FIG. 5) is performed.

If a user has a collection of replaceable modules for implementing a variety of functions, a step 66 of deciding whether the present configuration serves the present needs may be performed. If OK, the process is stopped 67, and if the present configuration is not suitable, steps 64 and 65 are repeated. The latter process of deciding whether the present configuration serves the present needs may alternatively be initiated from point 68, which represent a normal case of a user wondering whether the device as it is conforms to the requirements of the situation.

If the device is assembled by a producer or supplier of the device, it may be of interest to ensure that the user is not able to detach the modules and assemble them again (by mechanically or electronically 'lock' them together) in order for the producer or supplier to be able to guarantee the correct function of the device.

Alternatively, a check procedure may be implemented by each power up of the device.

Some preferred embodiments have been shown in the foregoing, but it should be stressed that the invention is not limited to these, but may be embodied in other ways within the subject matter defined in the following claims. For example, above the electronic means for controlling the medication delivery process, etc., were part of a basis module. It might as well be part of a replaceable module, possibly, if convenient and/or economical, divided in several replaceable modules. Likewise, in the above embodiments only one basis module is referred to. However, one of a selection of several different basis modules may form the core of the medication delivery device (e.g. including more or less basic electronics such as electro-acoustic interface, special power supplies etc.).

What is claim is:

1. A hand-held medical apparatus for assisting in the medical self-treatment of a user, the apparatus comprising:

a basis module comprising a processor and power source;

a first replaceable module that is mechanically and electronically interfaceable with the basis module;

a second replaceable module that is mechanically and electronically interfaceable with the basis module;

wherein, the basis module comprises a user input means, a display means and wherein the processor of the basis module sends commands to the replaceable modules and receives output from the replaceable module and displays that output, and wherein the first and second replaceable modules require processing resources from the basis module in order to assist the user in medical self-treatment;

wherein the basis module comprises a medication injection device comprising:

a holder for holding a cartridge of medication, the cartridge being of the type having a moveable piston;

a piston rod for engaging the piston in the cartridge and for driving a dose from the cartridge by moving the piston a predetermined distance;

an electromechanical piston rod drive; and wherein the processor is configured to control the piston rod drive.

2. A hand-held medical apparatus according to claim 1, wherein the processor is configured to perform a plurality of operations but limits access to some of the operations based on user identification.

3. A hand-held medical apparatus for assisting in medical self treatment, the apparatus comprising:
- a basis module that comprises:
  - an injection device having a processor, an electromechanical piston rod drive controlled by the processor and a cartridge of medication that a piston rod acts upon;
- a first replaceable module that is mechanically and electronically interfaceable with the basis module;
- a second replaceable module that is mechanically and electronically interfaceable with the basis module; and
- wherein, the basis module comprises a user input, and a display wherein the processor of the basis module sends commands to the replaceable modules and receives output from the replaceable modules and displays that output, and wherein the first and second replaceable modules require processing resources from the basis module in order to assist the user in medical self-treatment.

* * * * *